(12) United States Patent
Li et al.

(10) Patent No.: US 6,482,428 B1
(45) Date of Patent: Nov. 19, 2002

(54) WEIGHTED EYELID IMPLANT

(76) Inventors: Philip S Li, 239-56 66th Ave., Douglaston, NY (US) 11362; Curtis D Lenox, 86-44 56th Ave., apt. 3A, Elmhurst, NY (US) 11373

(*) Notice: Subject to any disclaimer, the term of this patent is extended or adjusted under 35 U.S.C. 154(b) by 22 days.

(21) Appl. No.: 09/928,874

(22) Filed: Aug. 13, 2001

(51) Int. Cl.[7] ................................................. A61F 2/14
(52) U.S. Cl. ......................................... 424/427; 623/4
(58) Field of Search ............................... 424/427, 428; 623/4

(56) References Cited

U.S. PATENT DOCUMENTS 4,595,713 A * 6/1986 St. John
5,137,728 A * 8/1992 Bawa
5,164,188 A * 11/1992 Womg
5,542,437 A * 8/1996 Blackmore et al. ......... 128/899

* cited by examiner

*Primary Examiner*—Carlos Azpuru
(74) *Attorney, Agent, or Firm*—Michael I. Kroll (57) ABSTRACT

A weighted upper eyelid implants for assisting and achieving complete eyelid closure and partial recreation of a natural blinking reflex. The implant is formed of a main plate having suture channels extending partially therethrough for receiving a suture knot tied in a suture passing through an adjacent suture hole thereby securing the weighted implant to the eyelid while preserving a cosmetically pleasing image.

21 Claims, 7 Drawing Sheets

WEIGHTED EYELID IMPLANT

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A SEQUENCE LISTING, A TABLE OR A COMPUTER PROGRAM LISTING APPENIDX SUBMITTED ON A COMPACT DISC

Not Applicable

BACKGROUND OF THE INVENTION

1. Field of the Invention

The present invention relates generally to eyelid implants, and more specifically, to weighted upper eyelid implants for assisting and achieving complete eyelid closure and partial re-creation of a natural blinking reflex.

2. Description of the Prior Art

Numerous types of eyelid implants have been provided in the prior art. For example U.S. Pat. Nos. 5,137,728, 4,595,713, and 5,164,188 all are illustrative of such prior art. While these units may be suitable for the particular purpose to which they address, they would not be as suitable for the purposes of the present invention as heretofore described.

U.S. Pat. No. 5,137,728

Inventor: Rajan Bawa

Issued: Aug. 11, 1992

An ocular insert for insertion into the cul de sac of the eye which is a substantially circular disc having a concave posterior surface and a convex anterior surface with a radius of curvature less than that of the sclera and a center thickness of less than about 1.5 mm U.S. Pat. No. 4,595,713

Inventor: Kenneth St. John

Issued: Jun. 17, 1986

A medical implant useful in the regeneration of soft and hard connective tissue, such as cartilage and bone, is disclosed which comprises a copolymer of a major amount of epsilon caprolactone and a minor amount of lactide. Where regeneration of bone tissue, in particular, is desired, the copolymer may further include osteogenic material in powdered or particulate form. If soft tissue regeneration is desired, the copolymer may include chopped carbon fiber. A mass of the copolymer, optionally including additives, may be molded by hand by heating the polymer to a temperature of 115°–160° F., by, for example, immersion in hot water. The mass is then molded to the void to be filled or shape the regenerated tissue is desired to assume, and implanted in the patient. The mass is gradually U.S. Pat. No. 5,164,188

Inventor: Vernon G. Wong

Issued: November 17, 1992

Encapsulated agents are employed for introduction into the suprachoid of an eye for therapeutic purposes. The administration of drugs is controlled and maintained for long periods of time, while ensuring the substantial absence of significant levels outside the site of administration.

SUMMARY OF THE PRESENT INVENTION

The present invention relates generally to eyelid implants and, more specifically, to weighted upper eyelid implants formed from a non-reactive metal with suture channels for the purpose of assisting complete closure of the upper eyelid and re-creation of a natural blinking reflex while maintaining a cosmetically pleasing appearance.

A primary object of the present invention is to provide an eyelid implant that will overcome the shortcomings of prior art devices.

Another object of the present invention is to provide an eyelid implant having suture channels carved therein.

A further object of the present invention is to provide an eyelid implant that is weighted and formed from a non-reactive metal such as gold.

A yet further object of the present invention is to provide an eyelid implant wherein the suture channels are for securing the implant to the tissue of the eyelid.

A still further object of the present invention is to provide an eyelid implant able to assist in complete closure of the eyelid.

An even further object of the present invention is to provide an eyelid implant for partially re-creating a natural blinking reflex.

A yet further object of the present invention is to provide an eyelid implant which eliminate cosmetically displeasing suture lines on the exterior of the eyelid.

Another object of the present invention is to provide an eyelid implant weighing between substantially 0.6 grams and substantially 2.6 grams.

An even further object of the present invention is to provide an eyelid implant having a thickness of substantially 1.0 millimeters or less.

Another object of the present invention is to provide an eyelid implant wherein the suture channels have a depth of substantially 400 microns.

Additional objects of the present invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views.

DESCRIPTION OF THE REFERENCED NUMERALS

Turning now descriptively to the drawings, in which similar reference characters denote similar elements throughout the several views, the Figures illustrate the eyelid implant having suture channels of the present invention. With regard to the reference numerals used, the following numbering is used throughout the various drawing figures.

10 eyelid implant having suture channels and suture holes of the present invention
12 main body of the implant
13 bottom side of the body of the implant
14 a first suture hole
15 top side of the body of the implant
16 a first suture channel
17 bottom edge of main body
18 a second suture channel
19 top edge of main body
20 a second suture hole
22 a third suture hole
24 a third suture channel
26 column indicating weight of the eyelid implant
28 column indicating number of suture holes
30 column indicating length
32 column indicating width
34 column indicating thickness
36 base of suture channel
38 first side of suture channel
40 second side of suture channel

DETAILED DESCRIPTION OF THE PREFERRED EMBODIMENT

Turning now descriptively to the drawings, in which similar reference characters denote similar elements throughout the several views, FIGS. 1 through 7 illustrate the eyelid implant of the present invention indicated generally by the numeral 10.

Figure 1:
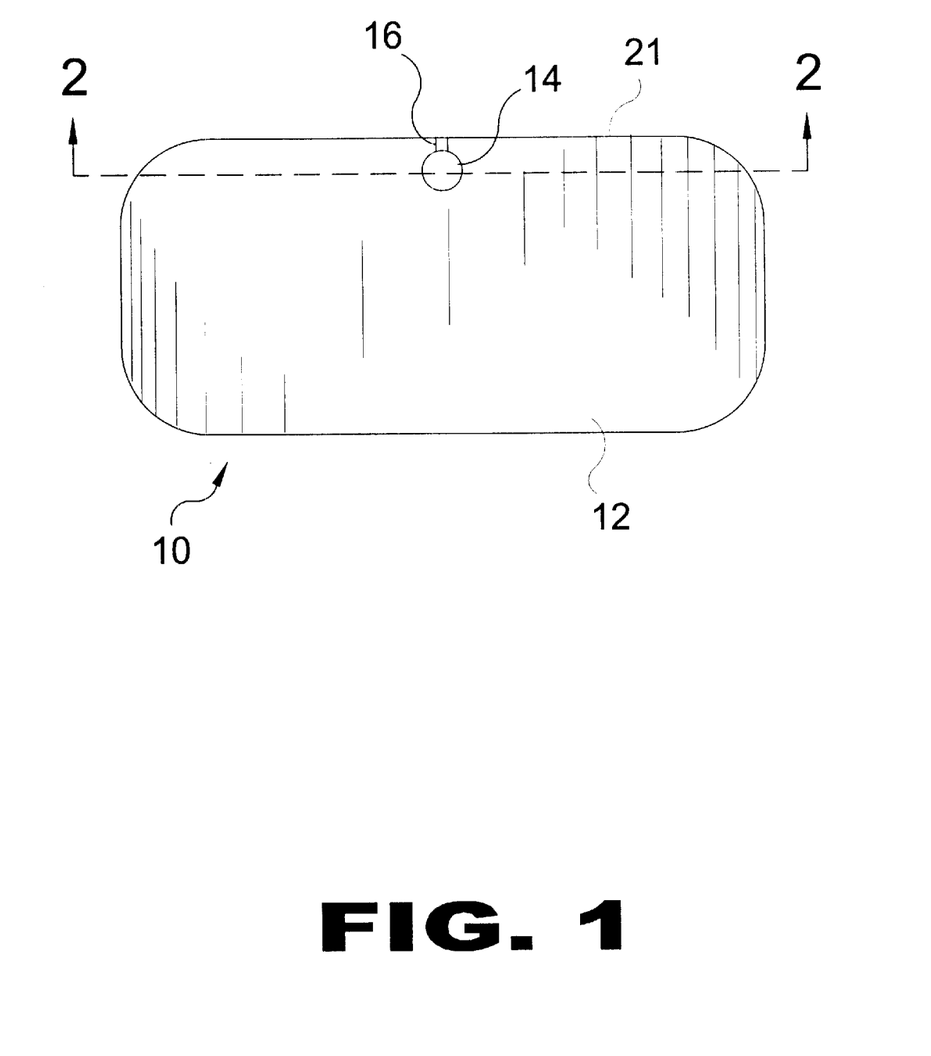
FIG. 1 is a top view of the eyelind implant of the present invention with one suture channel and one suture hole.

FIG. 1 is a top view of the eyelid implant 10. The eyelid implant 10 includes a main body 12. The main body 12 is formed from a non-reactive metal. Preferably, the main body is formed from gold. However, any non-reactive metal may be used to form the eyelid implant as long as the metal is able to form an eyelid weight having a desired size and weight while not causing a negative reaction with the user when implanted in the eyelid. Shown herein is the top side 15 of the main body 12. The main body 12 of the eyelid implant 10 has a first suture hole 14. The first suture hole 14 extends through the main body 12 of the implant 10. The main body 12 of the eyelid implant 10 also contains a first suture channel 16. The first suture channel 16 is carved into the top side 15 of the main body 12 of the eyelid implant 10 and positioned adjacent to the first suture hole 14. The first suture channel is formed of a base 36 having a first and second side, 38 and 40 respectively. The first and second sides 38 and 40, respectively, of the suture channel preferably extend parallel to each other. The first and second parallel sides 38 and 40, respectively, are perpendicular to the base. However, the suture channel may be of any dimensions and shape able to retain the suture therein upon securing of the eyelid implant within the eyelid of the user's eye. The first suture channel 16 preferably has a depth substantially equivalent to 400 microns. However, the first suture channel 16 may be of any depth able to provide a recess for receiving a suture knot while losing off the first suture hole 14 and not extending completely through the main body 12. The first suture channel 16 and first suture hole 14 are preferably positioned substantially at the midpoint along a top edge 21 of the main body 12 of the implant 10.

Figure 2:
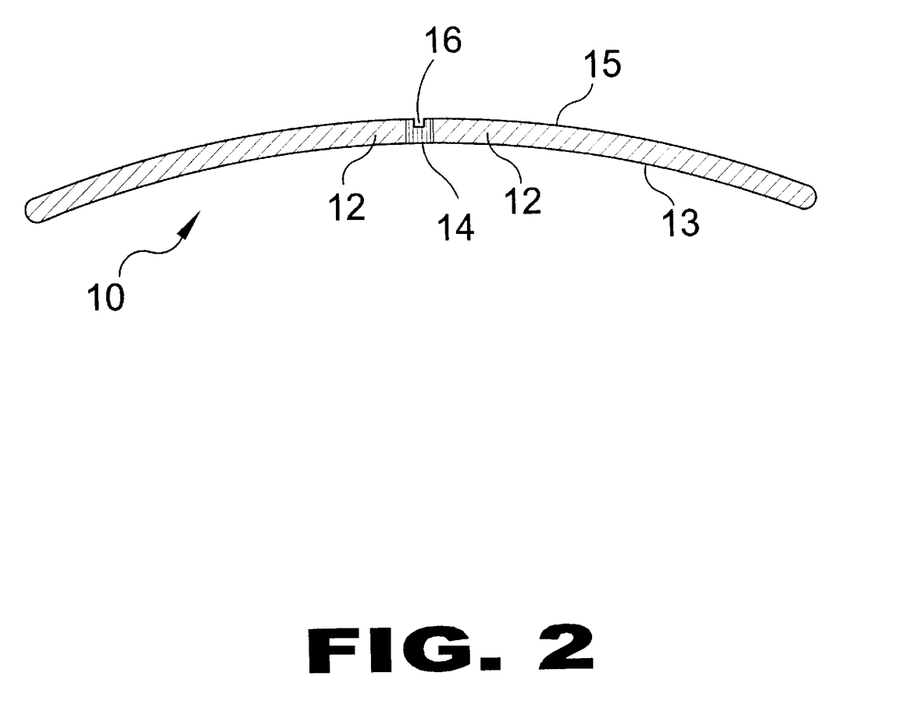
FIG. 2 is an cross sectional view of the eyelid implant having one suture channel and one suture hole taken along the line 2—2 of FIG. 1.

FIG. 2 is a cross sectional view of the eyelid implant taken along the line 2—2 as seen in FIG. 1. The main body 12 of the implant 10 has a top side 15 and a bottom side 13. The main body 12 has an arcuate shape and is substantially similar to that of an eye of a user therefore providing a natural fit to the eye of a user when implanted. The first suture channel 16 extends partially through the main body 12 of the implant 10. Preferably the depth of the first suture channel 16 is substantially 400 microns. However, the suture channel 16 may extend to any depth without extending completely through the main body 12. The first suture channel 16 is positioned at a mid point along a length of the main body 12. The first suture hole 14 is positioned adjacent the first suture channel 16 and preferably at a tangent to the first suture channel 16 whereby the first suture channel 16 closes the first suture channel 14.

Figure 3:
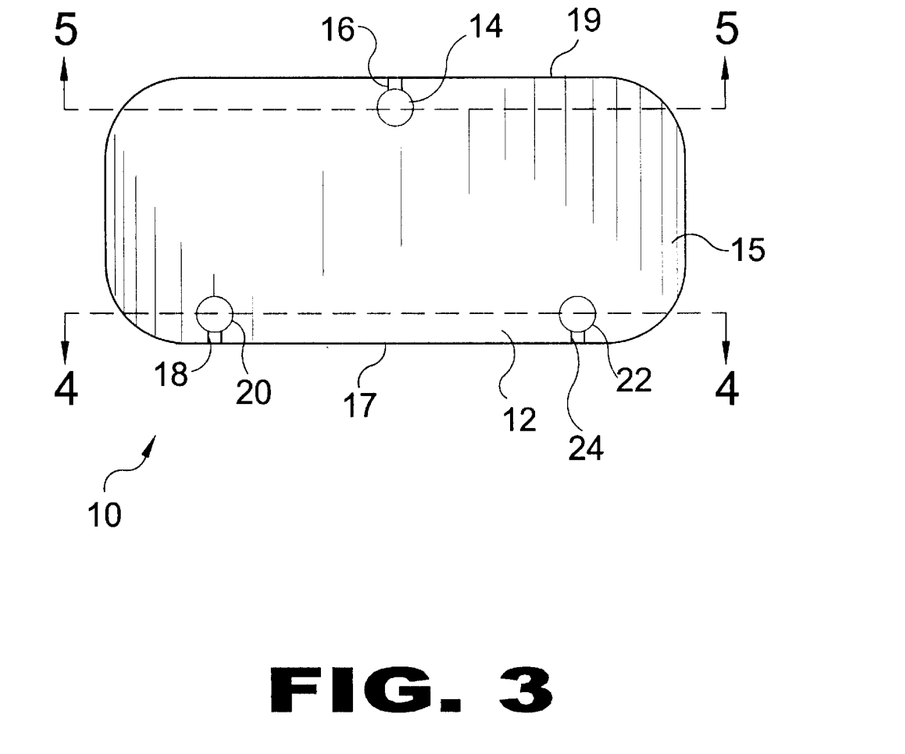
FIG. 3 is a top view of the eyelid implant of the present invention having three suture channels and three suture holes.

FIG. 3 is a top view of an alternate embodiment if the eyelid implant 10 of the present invention. The eyelid implant 10 is formed from a main body 12. The main body 12 is formed from a non-reactive metal. Preferably, the main body is formed from gold. However, any non-reactive metal may be used to form the eyelid implant as long as the metal is able to form an eyelid weight having a desired size and weight while not causing a negative reaction with the user when implanted. The main body 12 has a top side 15. The top side 15 includes a top edge 19 and a bottom edge 17. The main body 12 has a first suture channel 16 carved in the top side 15 of the main body 12 along the top edge 19. The first suture channel 16 extends preferably at least partially through the main body 12. The first suture channel 16 is preferably positioned at substantially a mid point of the main body 12 along the top edge 19. Positioned adjacent the first suture channel 16 in the main body 12 is the first suture hole 14. The first suture hole 14 extends entirely through the main body 12. Positioned along the bottom edge 17 of the top side 15 of the main body 12 are second and third suture channels, 18 and 24 respectively, and second and third suture holes, 20 and 22 respectively. The second suture channel 18 is carved into the top side 15 of the main body 12 along the bottom left edge of the main body 12. Positioned adjacent thereto is the second suture hole 20. The third suture channel 24 is carved into the top side 15 of the main body 12 along the bottom right edge of the main body 12. Positioned adjacent the third suture channel 24 is the third suture hole 22. Both the second suture hole 20 and third suture hole 22 extend completely through the main body 12 of the eyelid implant 10. Further, the first suture channel 16, second suture channel 18, and third suture channel 24 extend partially through the main body 12. The first suture channel 16, second suture channel 18, and third suture channel 24 preferably extend to a depth of substantially 400 microns. However, the first suture channel 16, second suture channel 18, and third suture channel 24 may extend to any desired depth without extending completely through the main body 12.

Figure 4:
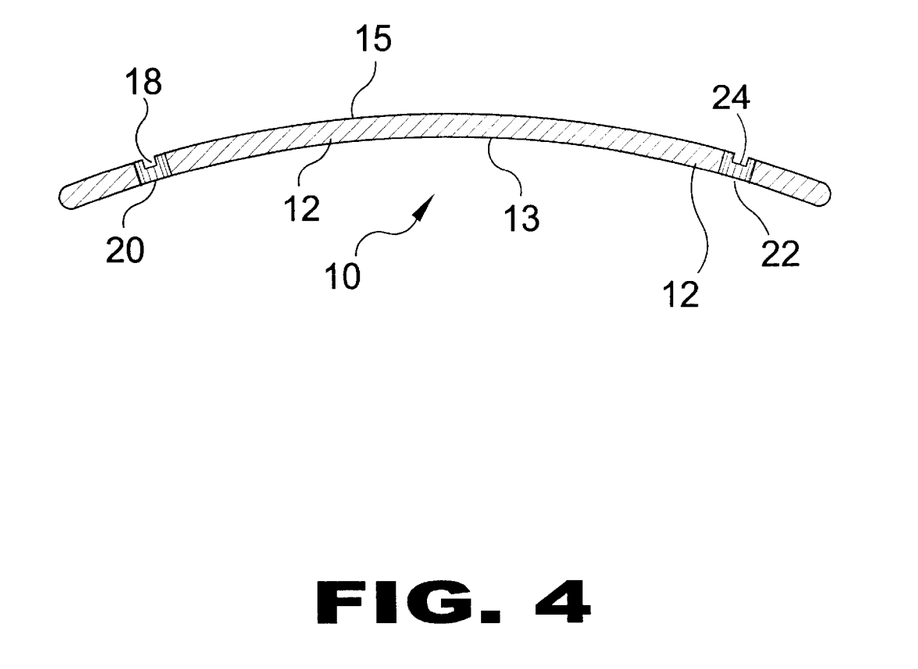
FIG. 4 is an cross sectional view of the eyelid implant of the present invention having three suture channels and three suture holes taken along the line 4—4 of FIG. 3.

FIG. 4 is a cross sectional view of the eyelid implant 10 taken along the line 4—4 as seen in FIG. 3. This view shows the shape of the eyelid implant 10. The implant 10 has a top side 15 and a bottom side 13. The main body 12 has an arcuate shape and is substantially similar to that of an eye of a user therefore providing a natural fit to the eye of a user when implanted. This cross sectional view shows the second suture channel 18 positioned on the left side of the main body 12. Further depicted is the third suture channel 24 positioned on the right side of the main body 12. The second and third suture channel, 18 and 24 respectively, extend partially through the main body 12 of the implant 10. Preferably, the depth of the second and third suture channels, 18 and 24 respectively, are each substantially 400 microns. However, the second and third suture channels, 18 and 24 respectively, may extend to any depth without extending completely through the main body 12. The second suture hole 20 is positioned adjacent the second suture channel 18 and preferably at a tangent to the second suture channel 18 whereby the second suture channel 18 closes the second suture hole 20. The third suture hole 22 is positioned adjacent the third suture channel 24 and preferably at a tangent to the third suture channel 24 whereby the third suture channel 18 closes a side of the third suture hole 20.

Figure 5:
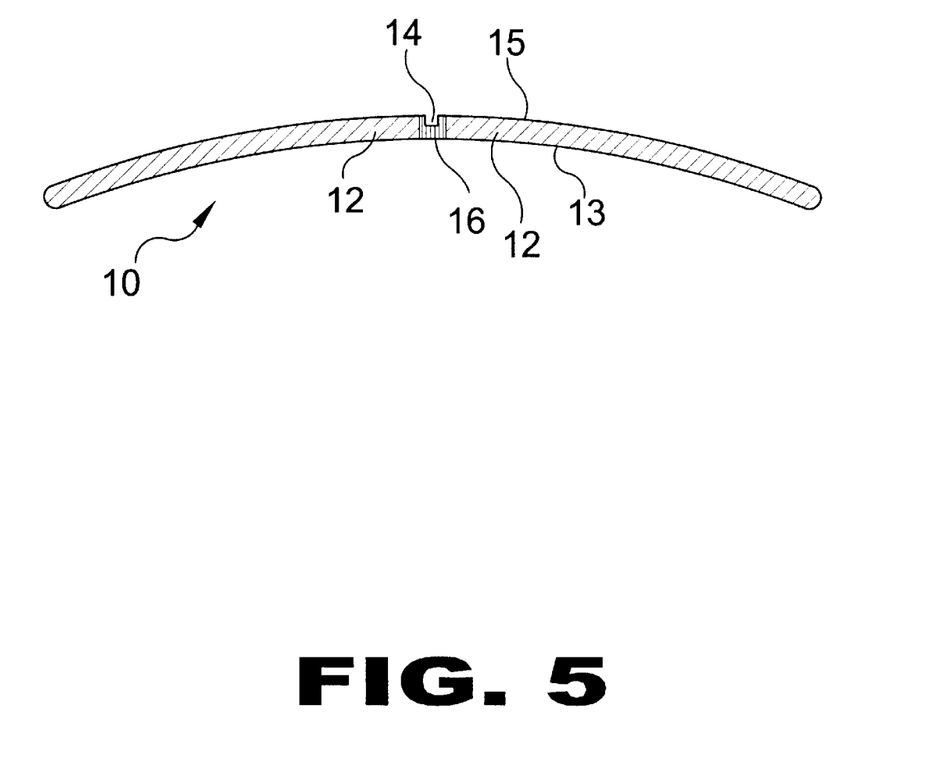
FIG. 5 is an cross sectional view of the eyelid implant of the present invention having three suture channels and three suture holes taken along the line 5—5 of FIG. 3.

FIG. 5 is a cross sectional view of the eyelid implant 10 taken along the line labeled 5—5 in FIG. 3. This view shows the main body 12 with the top side 15 and bottom side 13. The main body 12 has an arcuate shape and is substantially similar to that of an eye of a user therefore providing a natural fit to the eye of a user when implanted. The first suture channel 16 is shown extending partially through the main body 12 of the implant 10. Preferably, the depth of the first suture channel 16 is substantially 400 microns. However, the suture channel 16 may extend to any depth less than completely through the main body 12. The first suture channel 16 is positioned at the midpoint of the main body 12. The first suture hole 14 is positioned adjacent the first suture channel 16 and preferably at a tangent to the first suture channel 16 thereby closing a side of the first suture hole 14.

Figure 6:
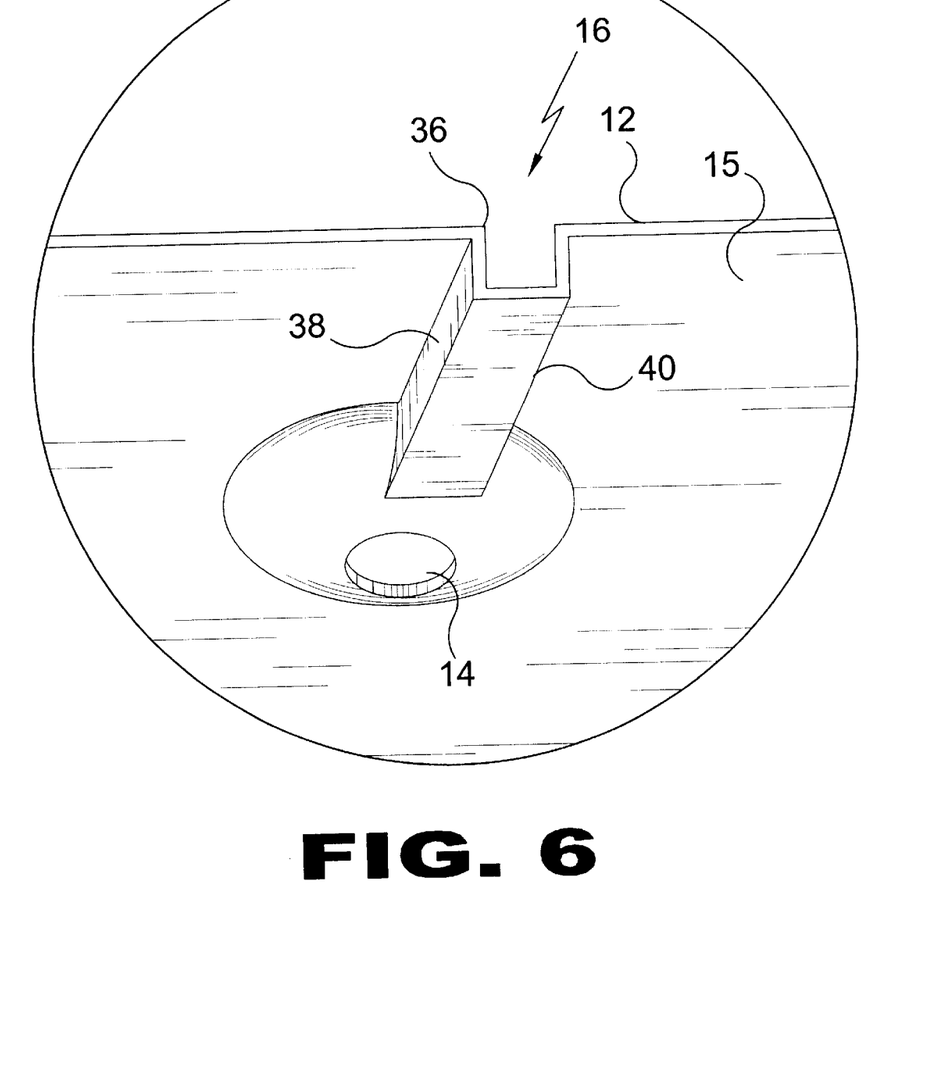
FIG. 6 is an enlarged top perspective view of a suture channel and suture hole of the eyelid implant of the present invention.

FIG. 6 is an enlarged perspective view of the suture channel 16 and suture hole 14. The suture channel 16 is cut in the top side 15 of the main body 12. Suture channel 16 is formed from a base 36, a first side 38 and a second side 40. The first side 38 preferably extends parallel to the second side 40. The first and second side, 38 and 40 respectively, are perpendicular to the base 36 and separated by a distance substantially equal to the diameter of a suture extending therebetween upon securing the eyelid implant 10 to the eyelid. The suture channel 16 extends from the edge of the main body 12 to the suture hole 14.

Figure 7:
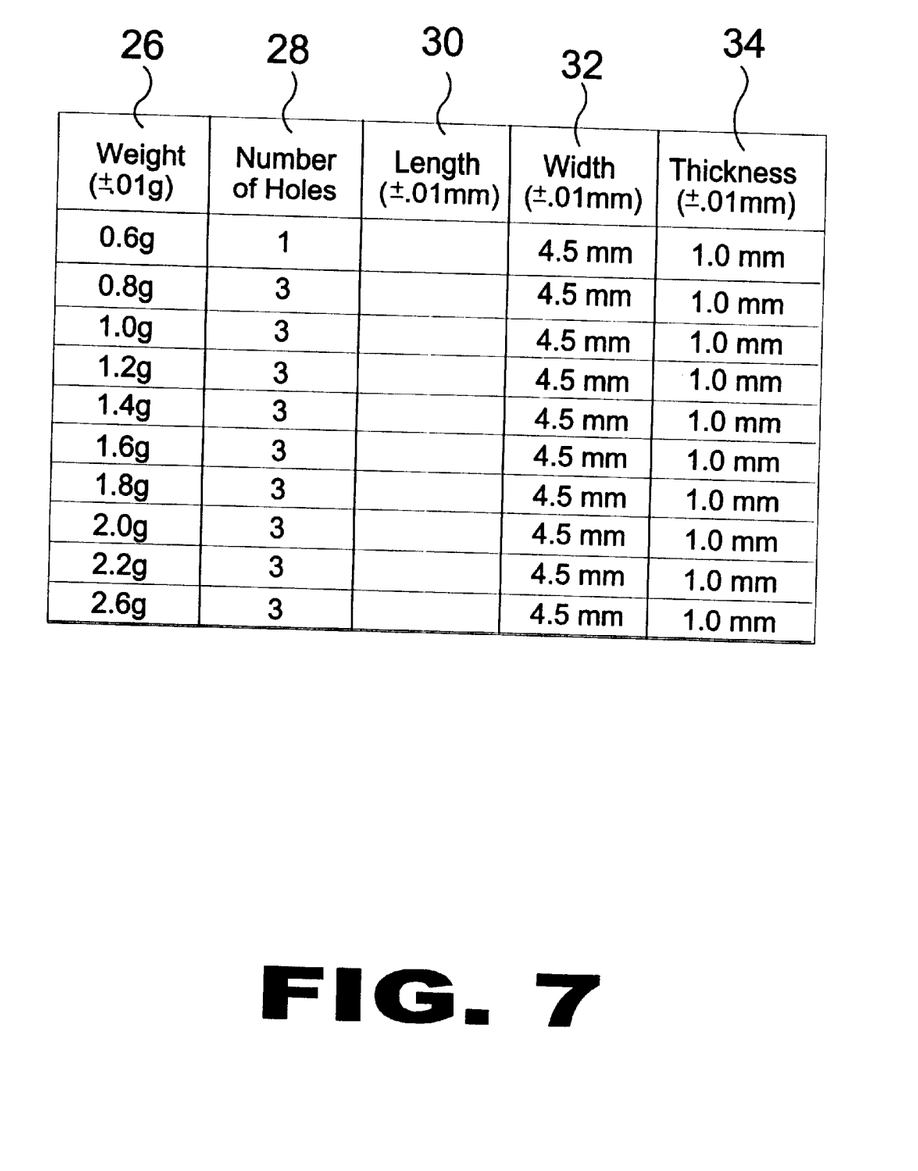
FIG. 7 is a table illustrating different properties of eyelid implants of the present invention.

FIG. 7 is a table of different properties associated with different eyelid implants. The column identified with the reference numeral 26 illustrates the different weights of the eyelid implants 10. Eyelid implants 10 range in weight from 0.6 grams to 2.6 grams. The weight amounts listed in the table increase in increments of 0.2 grams. The column identified with the reference numeral 28 shows the preferable number of suture holes present in eyelid implants of a respective eyelid implant 10. The column labeled with the reference numeral 28 illustrates that the number of suture holes present is based on the weight of the respective implant. Preferably implants 10 within a range between substantially 0.8 grams and 2.6 grams have three suture holes extending through the main body 12 of the implant 10. Implant 10 having a weight of 0.6 grams preferably have only one suture hole 28 extending therethrough. The column identified with the reference numeral 32 illustrates the width of the implant 10 and the column identified with the reference numeral 34 illustrates to the thickness of the implant 10 for each particular weight. All implants 10 discussed in the table have a width of substantially 4.5 millimeters and a thickness of substantially 1.0 millimeter or less. The column indicating the length of the eyelid implant 10 is identified by the reference numeral 30 and shows each respective implant 10 is based on the size of the individuals eyelid and is custom made for each individual user.

The operation of the eyelid implant 10 of the present invention will now be described with reference to the figures. In operation, the implant 10 is placed in the upper eyelid of the person for which it is designed and fitted. The result of implantation is a partial recreation of the natural blinking reflex. When a person who has the weighted eyelid implants relaxes his or her eyes, the additional weight of the eyelid implant 10 and the effects of gravity on the eyelid implant causes the eyelid to close. The bottom side 13 of the eyelid implant 10 is positioned adjacent to the inner portion of the eyelid whereas the top side is positioned adjacent to the outer portion of the eyelid. The implant 10 is attached to the tarsal plate of the upper eyelid via the suture holes 14, 20, and 22. The eyelid implants 10 of the present invention have suture channels 16, 18, and 24 for reception of a knot in the suture once it is tied off. The suture channels 16, 18 and 24 have a diameter able to receive a 6.0 suture therein or substantially 400 microns. Upon reception thereof, the respective suture channel firmly couches the suture. Once secured, the passage of the suture through the suture holes 18, 20 and 22 of the eyelid implant 10 creates a secure attachment between the upper eyelid and the implant 10 thereby preventing any post-operative movement. Another intended result of the eyelid implants being secured via the suture holes 14, 20, 22 and suture channels 16, 18, 24 is a cosmetically pleasing appearance whereby no suture lines are visible on the external part of the upper eyelid.

From the above description it can be seen that the eyelid implants of the present invention is able to overcome the shortcomings of prior art devices by providing an eyelid implant that has suture channels which enables a stronger and immovable means of attachment to the upper eyelid. Furthermore, the eyelid implant of the present invention allows for a more cosmetically pleasing appearance by eliminating visible suture lines in the upper eyelid.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An eyelid implant comprising:
   a) a main body;
   b) at least one suture hole extending completely through said main body; and
   c) at least one suture channel, extending partially through said main body to a predetermined depth, wherein a suture is passed through said at least one suture hole for securing said eyelid implant to an eyelid of a user.

2. The eyelid implant as recited in claim 1, wherein said main body is formed from a non-reactive metal.

3. The eyelid implant as recited in claim 1, wherein said non-reactive metal is gold.

4. The eyelid implant as recited in claim 1, wherein said at least one suture channel is formed from a base, a first side and a second side, said first side being parallel to said second side, said first and second sides extending perpendicular to said base.

5. The eyelid implant as recited in claim 4, wherein said suture channel extends between an edge of said main body to said suture hole.

6. The eyelid implant as recited in claim 5, wherein said suture channel extends through said main body to a depth of substantially 400 microns for the purpose of securing the suture and to prevent movement of the implant.

7. The eyelid implant as recited in claim 1, wherein said main body further comprising a second suture hole and a third suture hole, said second and third suture holes extending completely through said main body.

8. The eyelid implant as recited in claim 7, wherein said main body further comprises a second suture channel and a third suture channel, said second and third suture channels having parallel boundaries extending partially through said main body to a predetermined depth for the purpose of securing the suture and to prevent movement of the implant.

9. An eyelid implant as recited in claim 1, wherein said at least one suture channel is positioned at a midpoint of said main body and along an edge of said main body.

10. An eyelid implant as recited in claim 9, wherein said at least one suture hole is adjacent to said at least one suture channel.

11. The eyelid implant as recited in claim 8, wherein said second and third suture channels are positioned along an edge of said main body opposite said first suture channel, said second suture channel being positioned at a left side of said opposite edge and said third suture channel being positioned along the right side of said opposite edge.

12. The eyelid implant as recited in claim 11, wherein said second suture hole is positioned adjacent said second suture channel.

13. The eyelid implant as recited in claim 11, wherein said third suture hole is positioned adjacent said third suture channel.

14. The eyelid implant as recited in claim 11, wherein said second and third suture channels extend partially through said main body to a depth of substantially 400 microns.

15. The eyelid implant as recited in claim 1, wherein said main body is arcuate in shape and is substantially similar to the shape of the eye of the user.

16. The eyelid implant as recited in claim 1, wherein said implant has a weight within a range of substantially 0.2 grams and substantially 2.6 grams.

17. The eyelid implant as recited in claim 1, wherein said implant has a width of substantially 4.5 millimeters and a thickness of substantially 1.0 millimeters or less.

18. The eyelid implant as recited in claim 1, wherein the length and weight of said implant is custom fit for each individual user.

19. A method for securing an eyelid implant within an eyelid of a user, said method comprising the steps of:
   a) positioning the eyelid implant beneath the eyelid of the user;
   b) securing said implant to the eyelid by passing a suture through both the eyelid and a suture hole;
   c) tying a knot in said suture; and
   d) resting said suture knot in a suture channel adjacent said suture hole.

20. The method as recited in claim 19, further comprising the steps of:
   a) securing said implant to the eyelid by passing a second suture through both the eyelid and a second suture hole extending through said eyelid implant;
   b) tying a knot in said second suture; and
   c) resting said suture knot in said second suture in a second suture channel corresponding to said second suture hole.

21. The method as recited in claim 20, further comprising the steps of:
   a) securing said implant to the eyelid by passing a third suture through both the eyelid and a third suture hole extending through said eyelid implant;
   b) tying a knot in said third suture; and
   c) resting said suture knot in said third suture in a third suture channel corresponding to said third suture hole.

* * * * *